(12) United States Patent
Ford (10) Patent No.: US 7,647,206 B2
(45) Date of Patent: Jan. 12, 2010

(54) SYSTEM AND METHOD FOR MONITORING STRUCTURES FOR DAMAGE USING NONDESTRUCTIVE INSPECTION TECHNIQUES

(75) Inventor: Robert G. Ford, Snohomish, WA (US)

(73) Assignee: The Boeing Company, Chicago, IL (US)

( * ) Notice: Subject to any disclaimer, the term of this patent is extended or adjusted under 35 U.S.C. 154(b) by 405 days.

(21) Appl. No.: 11/532,453

(22) Filed: Sep. 15, 2006

(65) Prior Publication Data
US 2009/0192727 A1 Jul. 30, 2009

(51) Int. Cl.
*G01N 29/00* (2006.01)
*G06F 17/40* (2006.01)

(52) U.S. Cl. .......................... 702/183; 702/34; 702/35; 73/583

(58) Field of Classification Search ................. 702/183, 702/34–36
See application file for complete search history.

(56) References Cited

U.S. PATENT DOCUMENTS

| | | | | |
|---|---|---|---|---|
| 5,195,046 A | * | 3/1993 | Gerardi et al. | ................. 702/35 |
| 6,399,939 B1 | * | 6/2002 | Sundaresan et al. | ...... 250/231.1 |
| 7,222,027 B2 | * | 5/2007 | Gorinevsky et al. | ........... 702/35 |
| 7,343,265 B2 | * | 3/2008 | Andarawis et al. | .......... 702/188 |
| 2005/0075800 A1 | * | 4/2005 | Batzinger et al. | ............. 702/35 |
| 2006/0106550 A1 | * | 5/2006 | Morin et al. | ................... 702/34 |
| 2006/0287842 A1 | * | 12/2006 | Kim | .......................... 702/183 |

OTHER PUBLICATIONS

Bulut et al.; "Real-time Nondestructive Structural Health Monitoring using Support Vector Machines and Wavelets"; Aug. 2004; Seattle, USA.
Sun et al.; "Statistical-based Structural Health Monitoring Using Wavelet Packet Transform". (No date provided).

* cited by examiner

*Primary Examiner*—Hal D Wachsman (57) ABSTRACT

A system and method for monitoring a structure for damage is provided. The method includes stimulating a sensor in a sensor array to generate a plurality of waves. The sensor array includes one or more quadrants, wherein each quadrant includes one or more sensors. Sensor data from all sensors are acquired in each quadrant in parallel. The sensor data wave characteristics is processed for analysis. The processed sensor data wave characteristics are compared with threshold values to determine the presence of damage to the structure. If the presence of damage is determined, a corrective system is notified for corrective action.

29 Claims, 9 Drawing Sheets

SYSTEM AND METHOD FOR MONITORING STRUCTURES FOR DAMAGE USING NONDESTRUCTIVE INSPECTION TECHNIQUES

CROSS REFERENCE TO RELATED APPLICATIONS

None

BACKGROUND

1. Field of Invention

The present invention relates generally to inspecting structures for damage, and more particularly to detecting structure damage by using a sensor array laid on the structure.

2. Background of the Invention

Certain structure failures may result in loss of property and life. For example, aircraft structure failures may be catastrophic. Hence, it's prudent to monitor such structures to avoid catastrophic failures.

Non-Destructive Inspection (NDI) techniques are used to monitor such structures. One such technique is based on propagating a wave through an aircraft structure and then observing the echo. This is achieved by placing a probe, containing an ultrasonic transducer, on the structure. The wave propagates through the aircraft in a Z-axis (i.e. the axis which is normal to the surface of the structure). This technique can only inspect a very small area of the aircraft. To monitor and detect damage on a large aircraft structure (for example the wing structure) will require a large number of sensors. This will also increase use of hardware and add weight to the inspection system.

In view of the above, what is needed is a method and system for efficiently monitoring a large area of a structure using one or more stimuli on a large number of sensors.

SUMMARY OF THE INVENTION

In one aspect of the present invention, a method for monitoring a structure for damage is provided. The method includes stimulating a sensor in a sensor array; wherein the sensor array includes one or more quadrants; wherein each quadrant includes one or more sensors; acquiring sensor data from all sensors in each quadrant in parallel; processing the sensor data for analysis; comparing the processed sensor data with threshold values to determine the presence of damage to the structure; and notifying a corrective system of the damage for corrective action.

In another aspect of the present invention, a method for monitoring a structure for damage is provided. The method includes (a) laying out a plurality of sensor arrays on the structure; wherein each of the plurality of sensor arrays includes a plurality of quadrants; wherein each quadrant in the plurality of quadrants includes a plurality of sensors; (b) continuously acquiring sensor data from all sensors in each quadrant in parallel; (c) processing the sensor data for analysis; (d) comparing the processed sensor data with threshold values; (e) repeating steps (b)-(d) until damage to the structure is detected; and (f) notifying a corrective system of the damage for corrective action.

In yet another aspect of the present invention, a system for monitoring a structure for damage is provided. The system includes a plurality of sensor arrays on the surface of the structure; wherein each sensor array in the plurality of sensor arrays includes a plurality of quadrants; and wherein each quadrant in the plurality of quadrants includes a plurality of sensors; and a plurality of network detection modules; wherein each network detection module in the plurality of network detection modules acquires sensor data from all sensors in each quadrant in parallel; wherein each network detection module includes a plurality of multiplexers for multiplexing the sensor data from each quadrant into a plurality of single channels with a single channel for each quadrant and a computational engine for comparing the plurality of single channels with predetermined thresholds to determine the presence of damage to the structure.

In yet another aspect of the present invention, system for monitoring a structure for damage is provided. The system includes a plurality of sensor arrays on the boundaries and between the structure; wherein each sensor array in the plurality of sensor arrays includes a plurality of quadrants; and wherein each quadrant in the plurality of quadrants includes a plurality of sensors; and a plurality of network detection modules; wherein each network detection module in the plurality of network detection modules acquires sensor data from all sensors in each quadrant in parallel; where each of the network detection modules are synchronized causing sensors on a first sensor array on a first boundary of the structure to acquire stimulus originating from a second sensor array on a second boundary of the structure; wherein each network detection module includes a plurality of multiplexers for multiplexing the sensor data from each quadrant into a plurality of single channels with a single channel for each quadrant and a computational engine for comparing the plurality of single channels with predetermined thresholds to determine the presence of damage to the structure.

This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

The foregoing features and other features of the present invention will now be described with reference to the drawings of a preferred embodiment. The illustrated embodiment is intended to illustrate, but not to limit the invention. The drawings include the following.

DETAILED DESCRIPTION OF THE PREFERRED EMBODIMENTS

The following detailed description is of the best currently contemplated modes of carrying out the invention. The description is not to be taken in a limiting sense, but is made merely for the purpose of illustrating the general principles of the invention, since the scope of the invention is best defined by the appended claims.

According to the present invention, a Structural Health Monitoring (SHM) System and method for monitoring a large area of a structure for damage using one or more stimuli for a sensor array is provided. Although the method of the present invention is implemented using an aircraft, those skilled in the art will recognize that the principles and teachings described herein may be applied to a variety of structures, including, but not limited to, buildings, automobiles, ships, helicopters, and trains.

The practicality and acceptance of the SHM System is dependent on achieving fast damage detection using Non-Destructive Inspection (NDI) techniques while minimizing the cost, weight and size of the system. The SHM system of the present invention places multiple sensor arrays on a structure and utilizes both active and passive structural damage detection. In active structural damage detection systems, a single sensor in a sensor array stimulates the structure under test while the other sensors in the sensor array measure the resultant structural response. This process continues until all sensors in all of the sensor arrays have been stimulated. In passive structural damage detection, sensors do not stimulate the structure; they simply monitor the structure to detect stress or loads beyond pre-determined limits.

Figure 1:
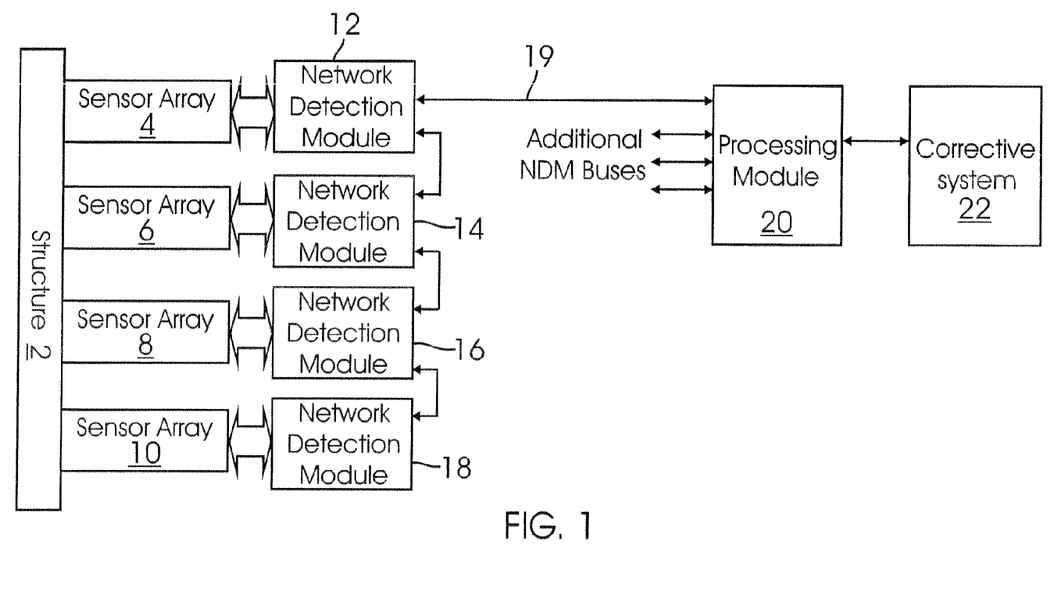
FIG. 1 illustrates a block diagram of a system for monitoring a large area of a structure for damage according to one aspect of the present invention.

Turning to FIG. 1, a block diagram of a SHM system 5 for monitoring a large area of a structure 2 for damage using a single stimulus on a large number of sensors, according to one aspect of the present invention is illustrated. In system 5, a plurality of sensor arrays 4, 6, 8, 10 are laid on the surface of structure 2 and connected to a plurality of network detection modules (NDMs) 12, 14, 16, 18 respectively. Each NDM 12, 14, 16, 18 provides a stimulus to a sensor in corresponding sensor arrays 4, 6, 8, 10 as well as the electrical interface necessary to capture or acquire the sensor data from sensor arrays 4, 6, 8, 10, i.e. the resultant structural response captured by all the other sensors in sensor arrays 4, 6, 8, 10. Although four NDMs and four sensor arrays are illustrated in FIG. 1, a greater or lesser number of NDMs and arrays may be utilized.

Damage is detected by comparing processed sensor data to threshold values stored in a processing module 20. Threshold values are based on allowable damage type and size for the type of structure from previous testing or from the prior occurrences of damage to the same type of structure. Processing module 20 instructs each NDM 12, 14, 16, 18 to send a stimulus to respective sensor arrays 4, 6, 8, 10, collect the sensor data and send the collected data to the processing module 20 then processing module 20 determines the presence of any damage on structure 2 by comparing the processed sensor data with the threshold values. Sensor data is transmitted from NDMs to processing module 20 using any known type of transmission 19, such as, wireless, Ethernet, and Fibre Channel.

Damage has occurred when the processed sensor data is equal to or greater than the threshold values. If damage is detected, processing module 20 notifies a corrective system 22, such as the airplane maintenance system, that there is a problem that requires correction.

A large area of structure 2 is inspected for damage using one or more stimuli on a large number of sensors. Instead of propagating the wave through structure 2 in the Z-axis as in the prior art, the present invention propagates the wave along the surface of structure 2 (i.e. Bulk, Rayleigh or Lamb waves in the x and y axis). The collected sensor data includes wave characteristics as the waves travel along the surface, i.e. reflections of the traveling waves, diffractions of the waves or a dispersion curve of the waves which indicates the nature or quality of the material or structure being inspected or monitored.

Figure 2:
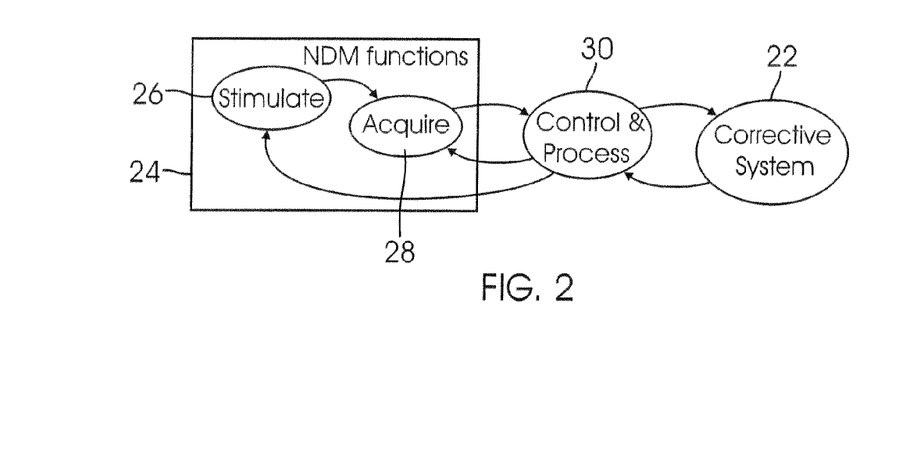
FIG. 2 is functional block diagram of the system and method for monitoring a structure for damage of FIG. 1.

FIG. 2 is a functional block diagram of the steps and processes of FIG. 1 used to capture, analyze and transmit the sensor data to corrective system 22. A NDM functional block 24 comprises a stimulate function 26 and an acquire function 28 for stimulating sensors and acquiring sensor data from surrounding sensors in the sensor arrays. A control and process function 30 instructs stimulate function 26 to stimulate a sensor in sensor arrays 4, 6, 8, 10 and instructs acquire function 28 to acquire or collect data from all sensors in sensor arrays 4, 6, 8, 10. The collected sensor data is processed in control and process function 30 to determine the presence of any damage on structure 2 and notify corrective system 22 of any damage.

Figure 3:
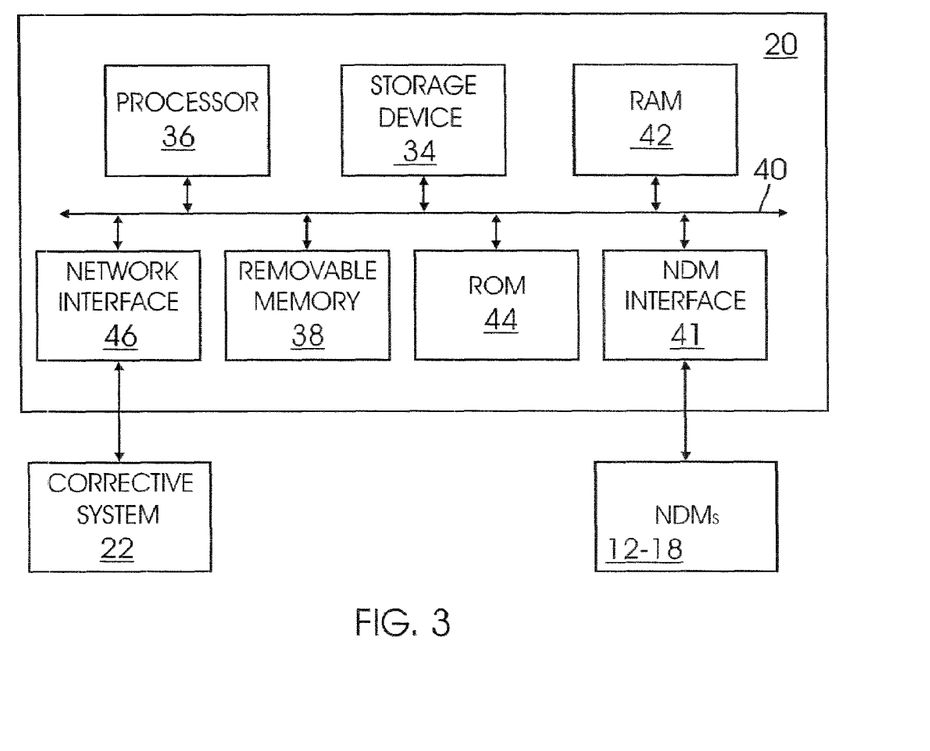
FIG. 3 is a top-level block diagram of a processing module according to one aspect of the present invention.

FIG. 3 is a block diagram of processing module 20, according to one aspect of the present invention. Processing module 20 includes a computer-readable memory storage device 34 for storing readable data. Storage device 34 may include a hard drive, a magnetic tape, a magnetic drum, integrated circuits, or the like, operative to hold data by any means, including magnetically, electrically, optically and the like. Storage device 34 stores operating system program files, application program files, computer-executable process steps of the present invention, web-browsers and other files. Some of these files are stored on storage device 34 using an installation program. For example, a microprocessor 36 executes computer-executable process steps of an installation program so that microprocessor 36 can properly execute the application program. Processing module 20 may also access computer-readable data files, application program files, and computer executable process steps embodying the present invention or the like via a removable memory device 38 (for example, a CD-ROM, a CD-R/W, a flash memory device, a Zip drive, a floppy disk drive, etc.). Microprocessor 36, storage device 34, and removable memory device 38 typically interface with a computer bus 40.

A CANBUS, AFDX, ARINC 429, ARJNC 629, modem, integrated services digital network (ISDN) connection, or the like (not shown) also provides processing module 20 with a network connection.

Also shown in FIG. 3 is an NDM interface 41, interfacing with computer bus 40 that operatively connects NDMs 12, 14, 16, 18 (as shown in FIG. 1) to processing module 20.

A random access memory ("RAM") 42 also interfaces with computer bus 40 to provide microprocessor 36 with access to random access memory. When executing stored computer-executable process steps from storage device 34, microprocessor 36 stores and executes the process steps out of RAM 42.

A read only memory ("ROM") 44 is provided to store invariant instruction sequences such as start-up instruction sequences or basic input/output operating system (BIOS) sequences. ROM 44 also interfaces with computer bus 40.

Processing module 20 can be connected to other computing systems and corrective system 22 through a network interface 46 using computer bus 40 and a network connection (not shown). Network interface 46 may be adapted to one or more of a wide variety of networks, including local area networks, storage area networks, wide area networks, the Internet, and the like.

In one aspect of the invention monitoring software may be supplied on a CD-ROM or a floppy disc, or alternatively it could be read from the network via network interface 46. In yet another aspect of the invention, processing module 20 can load the monitoring software from other computer readable media such as magnetic tape, a ROM, integrated circuit, or a magneto-optical disc. Alternatively, the monitoring software is installed onto storage device 34 of processing module 20 using an installation program, and it is executed using microprocessor 36.

The present invention is not limited to using a microprocessor, a reduced instruction set computer (RISC) processor or a hardware state machine may be used to determine the presence of damage to a structure.

In yet another aspect, the monitoring software may be implemented by using an Application Specific Integrated Circuit (ASIC) (not shown) that interfaces with processing module 20.

Figure 4:
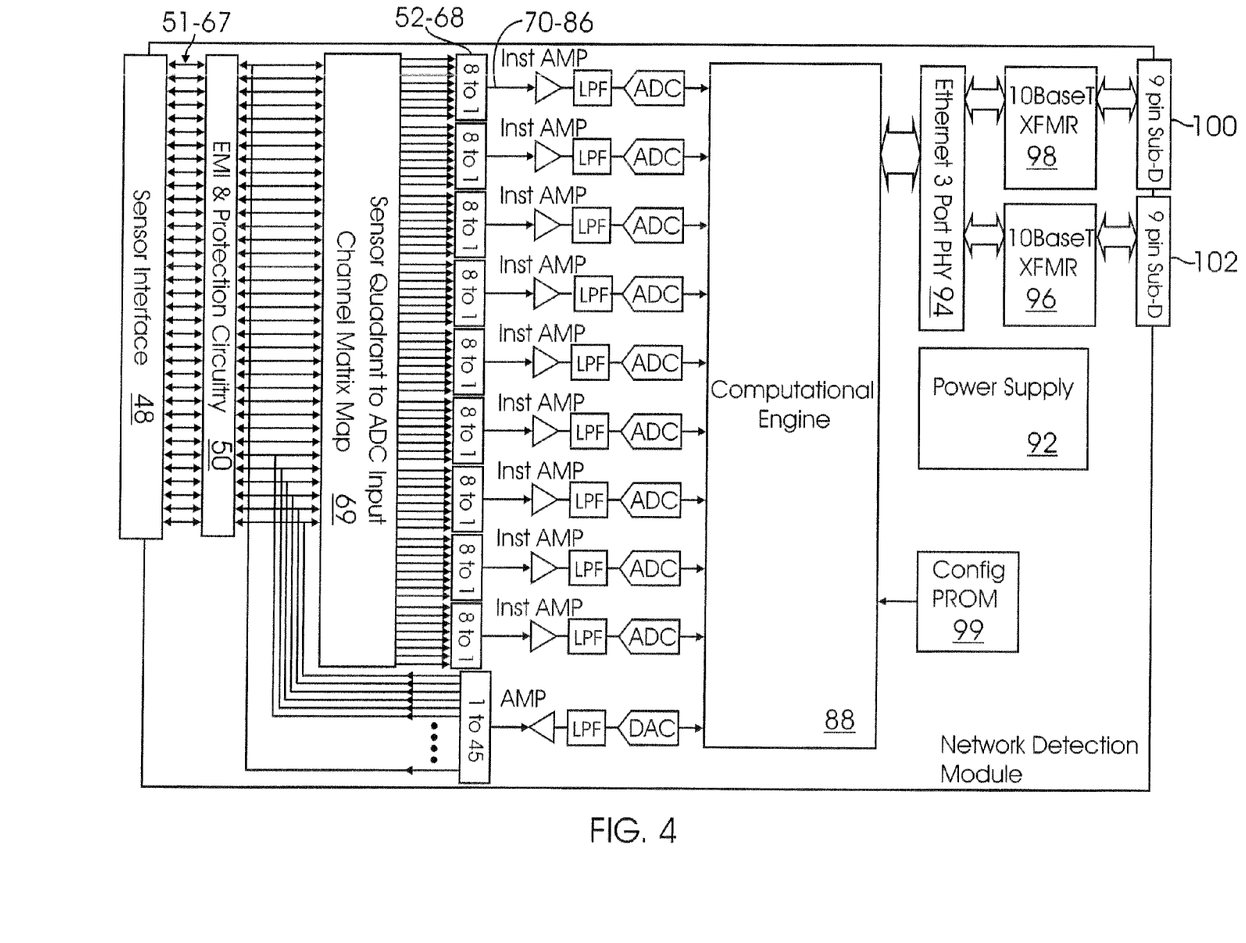
FIG. 4 illustrates the internal architecture of a network detection module, according to one aspect of the present invention.

FIG. 4 illustrates the internal architecture of a NDM, such as NDMs 12, 14, 16, 18 of FIG. 1, according to one aspect of the present invention. A distributed sensor interface 48 on the NDM is connected to a set of sensor arrays, such as sensor arrays 4, 6, 8, 10 in FIG. 1, on a structure. Sensor arrays contain a fixed maximum number of sensors, such as transducers, divided into fixed maximum number of quadrants (described below with reference to FIG. 5). The number of quadrants and transducers per quadrant are dependant on the size of the sensor or transducer array and the number of NDM transducer input channels.

In one aspect, there are nine transducers per quadrant and eight quadrants per array; however the number could be greater or smaller, depending on transducer layout and equipment constraints. Each NDM simultaneously acquires data from all transducers within each quadrant reducing the transducer acquisition time to less than 1 ms for each quadrant and less than 8 ms for an entire array in the case of nine transducers/quad and eight quads/array. As shown in FIG. 4, sensor interface 48 is connected to nine groups of transmission lines 51-67 with eight transmission lines in each group. Each transmission line in a group represents a different quadrant in an array.

Groups of transmission lines 51-67 are connected to a protection circuit 50 to protect against spikes in data and are then input into a sensor quadrant to ADC input channel matrix map 69. As there are only 45 unique inputs (as there are 45 sensors), matrix map 69 makes duplicate connections for sensors that are in one or more quadrants. For example, referring to FIG. 5 below, sensor 11 is located in quadrants Q0, Q1, Q4 and Q5. The duplicate connections are then input into a single input of a plurality of multiplexers 52-68, one multiplexer for each sensor array on the structure. The sensor data from each sensor array is multiplexed onto separate single channels 70-86 hence, a large parallel input captures data from nine channels/nine sensors simultaneously. Using single channels 70-86 allows for a more efficient means of communications, i.e., going to a higher speed bus with fewer wires and allowing data to be taken close to real time. Each of the single channels 70-86 is then transmitted through an amplifier; low pass filter (LFP) and an analog to digital (A/D) converter prior to being transmitted to a computational engine 88. A configured PROM 90 programs computational engine 88 for all NDM behavior. Ethernet port 94, transformers 96, 98 and connectors 100, 102 allow each NDM to communicate with processing module 20. Power supply 92 is used to power the NDMs.

Transducers are typically electro-mechanical conversion devices that convert mechanical strain or motion to electrical currents and/or voltages and vice-versa. Although in the preferred embodiment, the sensors are transducers, any sensor that results in a voltage or current source may be used and monitored.

Each NDM may operate simultaneously allowing all transducers attached to processing module 20 to be monitored in less than 10 ms during passive damage detection. All NDM activities are synchronized using a common, low-speed clock allowing the stimuli from one NDM to be acquired by surrounding NDMs during active damage detection. Transducers may also be monitored for extended periods of time, such as during monitoring for hard landing events of the aircraft, using a memory bank swap technique that allows transducer data to be stored for 30 seconds, and then swapped with another memory for another 30 seconds, while the first memory is uploaded to processing module 20. This process can be repeated until the memory limitations in processing module 20 are reached (greater than 30 minutes).

Figure 5:
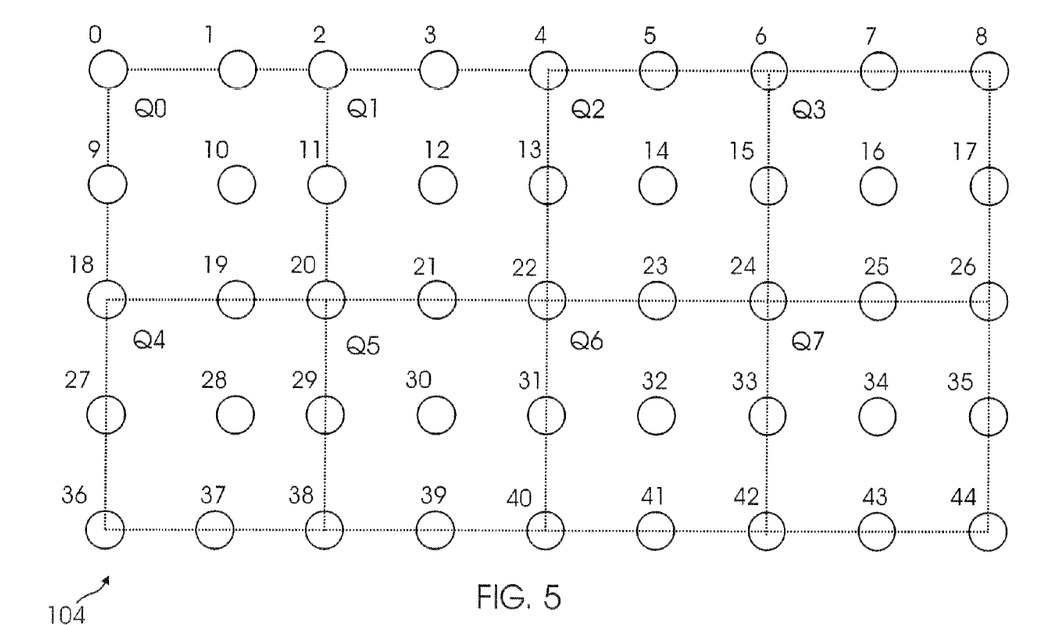
FIG. 5 illustrates an example of a transducer grid, according to one aspect of the present invention.
Figure 6:
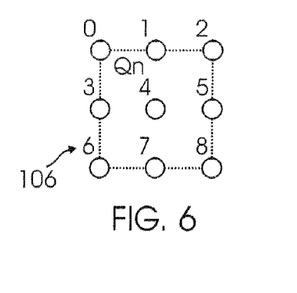
FIG. 6 illustrates an example of a quadrant in a transducer grid, according to one aspect of the present invention.

FIG. 5 illustrates an exemplary transducer array 104, according to one aspect of the present invention. Transducer array 104 comprises up to 45 sensors, 0-44 and is divided by the NDM into eight sections or quadrants Q0-Q7, where each quadrant provides nine transducers. FIG. 6 illustrates an example of a quadrant 106 in a transducer array, according to one aspect of the present invention. The NDM provides nine, parallel, input channels (groups of transmission lines 51-67 in FIG. 4) that are multiplexed to each quadrant.

Figure 7:
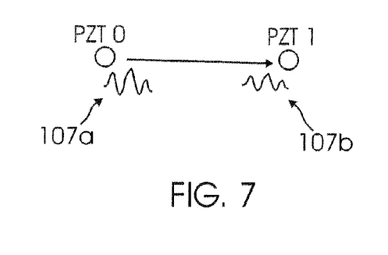
FIG. 7 illustrates an electronically stimulated sensor causing a structure to produce and propagate a surface wave to a second sensor.

Each NDM within system 5 stimulates a sensor in the sensor array and captures the wave data as it propagates through the structure. FIG. 7 illustrates an electrically stimulated sensor PZT0 causing the structure to produce and propagate a surface wave (or path) 107a to a second sensor PZT1. The characteristics of the propagated wave 107b when it arrives at sensor PZT1 contain information about this particular path in the structure. The system of the present invention uses all paths between all sensors to create a complete structural picture under the transducer array.

Figure 8:
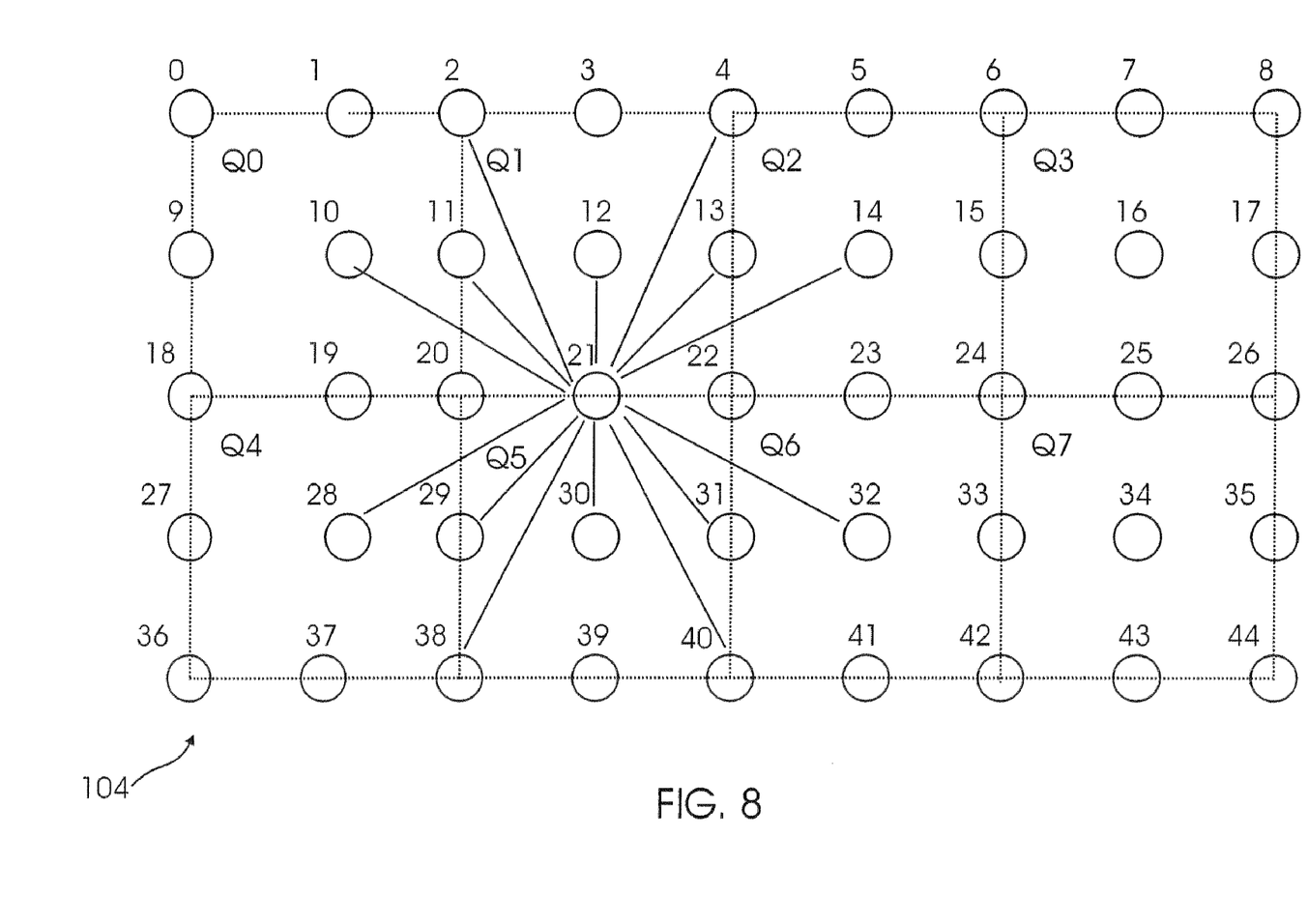
FIG. 8 illustrates an example of usable path data from a single stimulated sensor.

FIG. 8 illustrates an example of usable path data from a single stimulated sensor PZT21 in transducer array 104. When sensor PZT1 is stimulated 16 waves or paths are propagated. The NDM collects data from all 16 paths. As shown in FIG. 8, the 16 paths are: PZT21-PZT2; PZT21-PZT10; PZT21-PZT11; PZT21-PZT12; PZT21-PZT4; PZT21-PZT13; PZT21-PZT14; PZT21-PZT20; PZT21-PZT22; PZT21-PZT28; PZT21-PZT29; PZT21-PZT30; PZT21-PZF31; PZT21-PZT20; PZT21-PZT38; and PZT21-PZT40. It should be noted that all the sensors in transducer array 104 must be stimulated to get a complete picture of the structural health.

Figure 9:
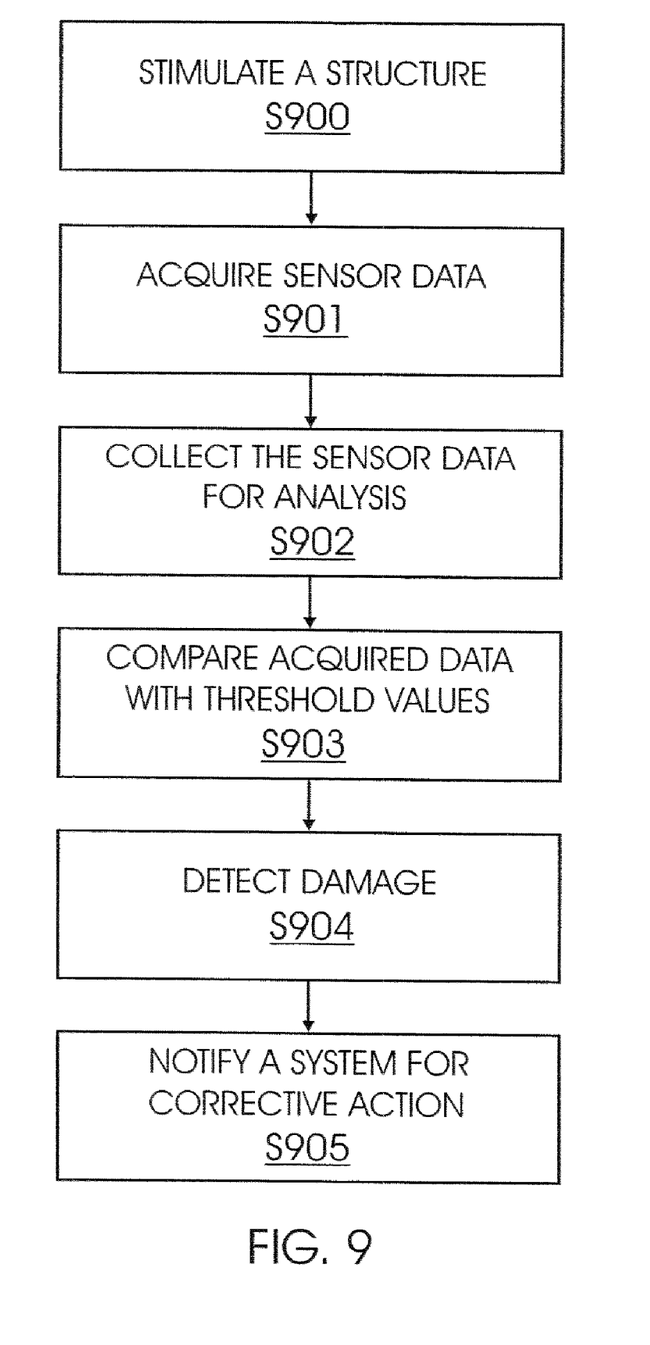
FIG. 9 is a flow chart for actively detecting structure damage, according to one aspect of the present invention.

FIG. 9 is a flow chart illustrating the steps for active interrogation, i.e. detecting structural damage using an active system, according to one aspect of the present invention. In step S900, a structure is stimulated by stimulating a sensor in a sensor array on the structure. A sensor is stimulated by applying a waveform to the sensor or transducer generating waves on the surface of the structure. In step S901, the sensor data is acquired using an echo or another sensor located some distance away. In other words, the structure is stimulated using a transducer and then that or another transducer acquires the data. Steps S900 and S901 are repeated until all sensors in all sensor arrays on the structure have been stimulated and the sensor data has been collected.

In step S902, the sensor data is collected by computational engine 88 and is uploaded to processing module 20 for analysis. The sensors may not transmit the data that is in a format readable by corrective system 22, which is where all the data goes. Computational engine 88 collects a series of data samples from each sensor that represents a waveform that has been captured over a period of time. That waveform will then be processed by processing module 20 to determine how fast the wave was traveling as well as determining if there were any echoes in the wave. For example, if a characteristic of a structural defect exists when a wave is propagating across it, a reflection from the beginning part of the defect and also from the back part will be seen. By propagating the wave in multiple directions, a composite can be built that shows the defect including the shape, using an intersection of all the reflections. The sensor data is being fused together into one picture of the structure.

In step S903, the acquired data is compared with the threshold values stored in the processing module to determine if there is damage to the structure. In step S904, based on the compared data, the presence of any damage is detected. Finally, in step S905, a corrective system is notified for corrective action. Notification can be to the aircraft maintenance system, an alarm, an email or a phone call to technician—service department.

Figure 10:
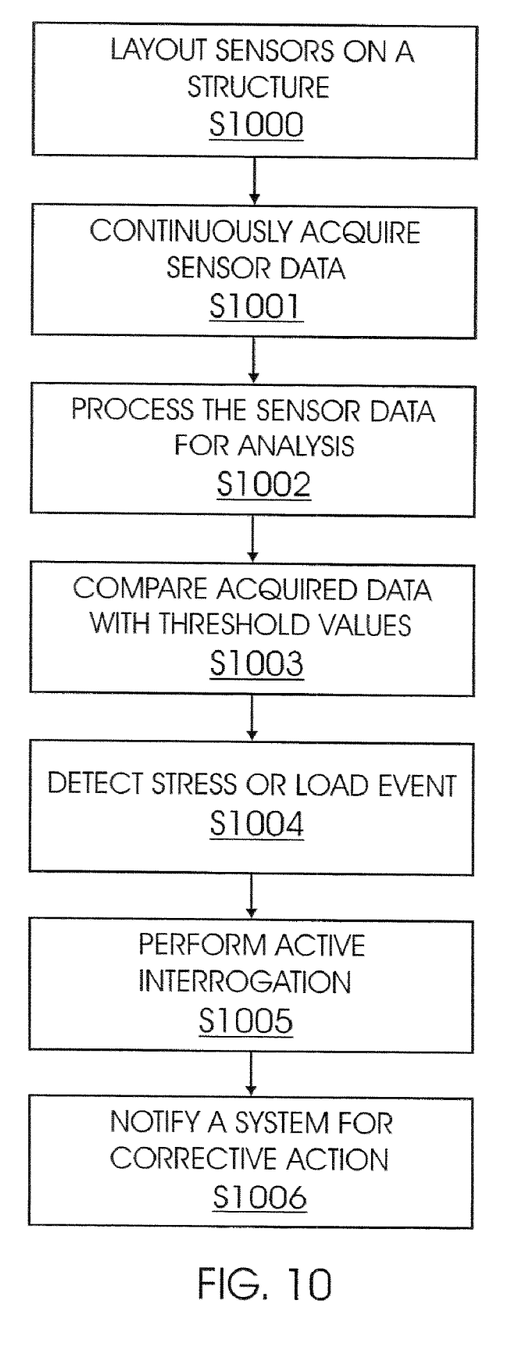
FIG. 10 is a flow chart for passively structure damage, according to one aspect of the present invention.

FIG. 10 is a flow chart illustrating the steps for detecting structure damage using a passive system, according to one aspect of the present invention. In a passive system, the system uses the same sensors as in the active system, but the structure is not stimulated. Instead, the sensors simply listen to the structure characteristics to detect any impact or stress event. For example, in an aircraft sitting on a tarmac, the sensors are monitoring around the cargo doors and if a truck or another vehicle came up and hit the side of the aircraft, the aircraft could detect the damage and either alerts the maintenance system or the crew or ground crew. If an impact or stress event was detected, an active interrogation, as described above with reference to FIG. 9, could be immediately performed to see what the level damage was, if any. The active and passive systems work together for maintaining the integrity of the area around the areas that are being monitored, such as doors.

Referring again to FIG. 10, in step S1000, sensors in the form of sensor arrays are laid out on a structure. In step S1001, sensor data is continuously acquired. In step S1002, the sensor data is processed for analysis. In step S1003, the acquired data is compared with the threshold values stored in processing module 20. In step S1004, based on the compared data, a determination of an impact or stress event is made. In step S1005 an active interrogation (as described above with reference to FIG. 9) is performed and compared with previously stored threshold levels to detect damage. Finally, in step S1006, a corrective system is notified for corrective action. Notification can be to the aircraft maintenance system, an alarm, an email or a phone call to technician—service department. The event is a high-energy impact, which can be estimated, based on the response from the sensors.

Figure 11:
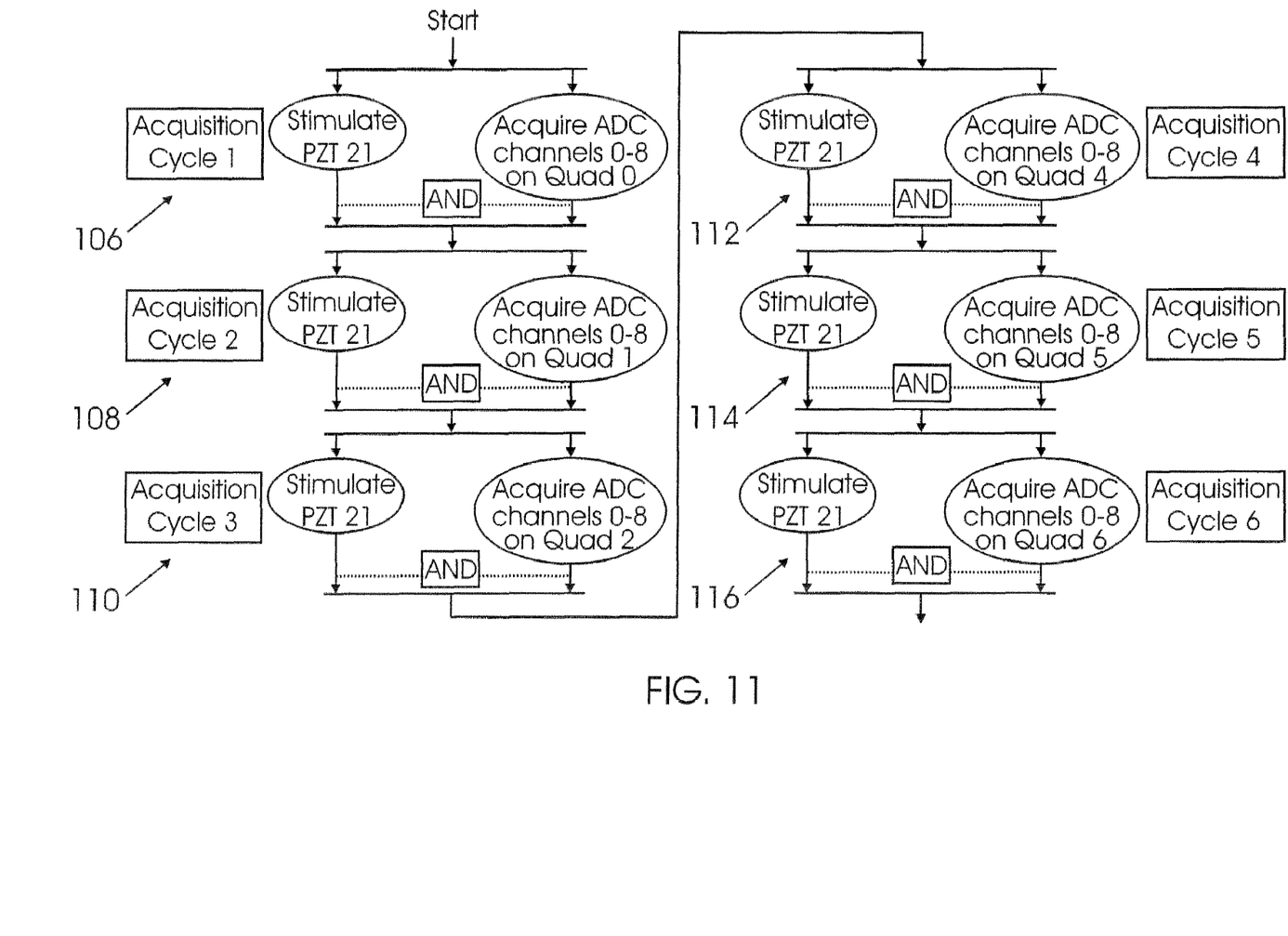
FIG. 11 illustrates an example of acquiring structural path data from a single sensor as illustrated in FIG. 8.

FIG. 11 illustrates an example of acquiring structural path data from a single sensor as illustrated in FIG. 8. The NDM accomplishes each path acquisition by stimulating transducer PZT21 and using nine input channels 0-8 to multiplex them amongst the eight quadrants. The stimulation of PZT21 is described with reference to FIG. 8. As can be seen in FIG. 8, six different quadrants have transducers from which data needs to be collected, Quad 0, Quad 1, Quad 2, Quad 4, Quad 5 and Quad 6; so six acquisition cycles are required 106-116. In acquisition cycle 1 106, PZT21 is stimulated and the nine input channels 0-8 on Quad 0 are acquired. In acquisition cycle 2 108, PZT21 is stimulated and the nine input channels 0-8 on Quad 1 are acquired. In acquisition cycle 3 110, PZT21 is stimulated and the nine input channels 0-8 on Quad 2 are acquired. In acquisition cycle 4 112 PZT21 is stimulated and the nine input channels 0-8 on Quad 4 are acquired. In acquisition cycle 5 114, PZT21 is stimulated and the nine input channels 0-8 on Quad 5 are acquired. In acquisition cycle 6 116, PZT21 is stimulated and the nine input channels 0-8 on Quad 6 are acquired.

The NDM accomplished all of the path data acquisitions in the example shown in FIG. 11 in six separate acquisition cycles, each taking about 341 us. For six quadrants, that's 2 ms total. All paths between 45 transducers can be stimulated and acquired in about 123 ms.

The same steps as described in FIGS. 8 and 11 are applied to each sensor in all the sensor arrays on the structure.

Since each NDM is independent in SHM system 5 of the present invention, all transducer arrays in an SHM System can be stimulated and acquired in the same time of 123 ms. So, the time required to interrogate a structure is independent of the number of transducer arrays in SHM System 5.

Prior art systems do the same path acquisition, but only work with two transducers at a time. So to accomplish the path acquisitions in FIG. 4, prior art systems would have to stimulate PZT 21, then acquire data on PZT 20, then Stimulate on PZT 21, then acquire data on PZT 10, and so forth until all 16 paths were acquired. Using the same path time of 341 us, it would take about 6 ms, three times longer. To capture all paths between 45 sensors (over 44 paths/stimulus×45 stimuli) would take 675 ms (5 times longer).

Figures 12, 13:
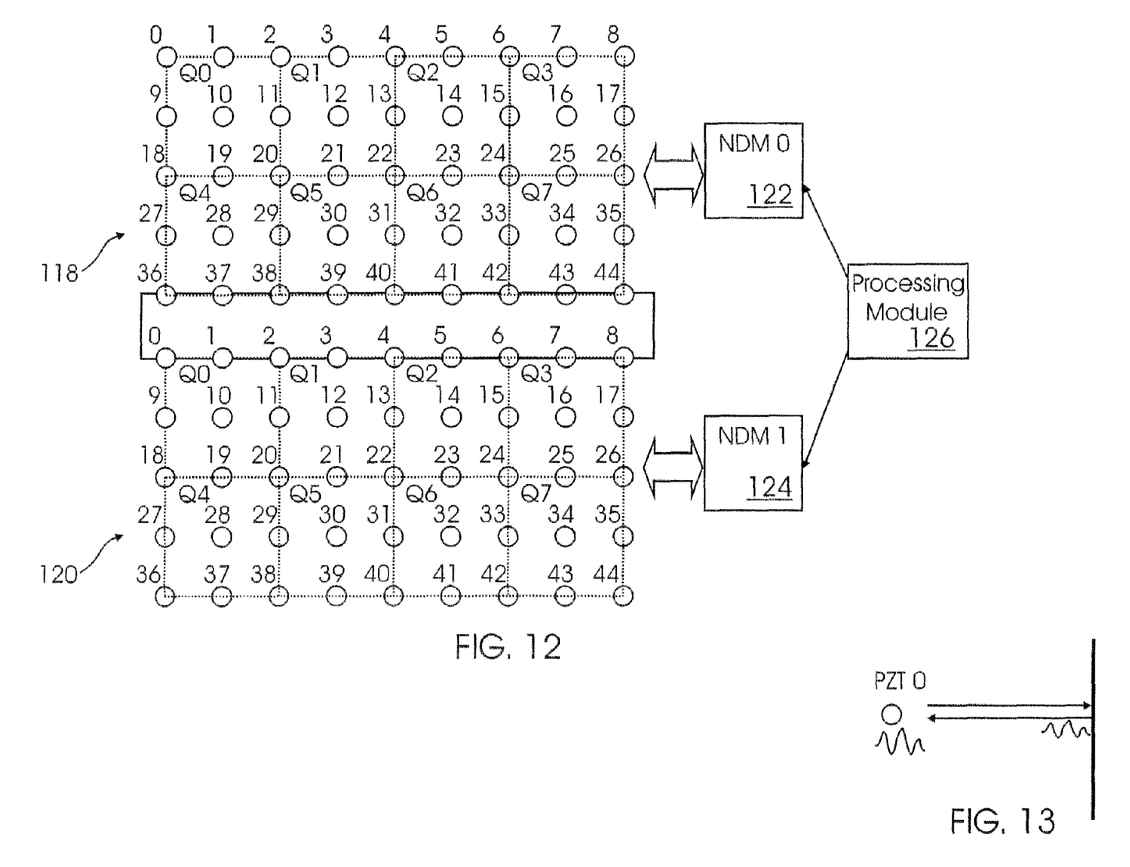
FIG. 12 illustrates an example of interrogating the structure between two or more adjacent transducer arrays, according to one aspect of the present invention.
FIG. 13 illustrates an example of pulse—echo acquisition, according to one aspect of the present invention.

FIG. 12 illustrates an example of interrogating a structure between two or more adjacent transducer arrays 118, 120. Each NDM 122, 124 stimulus and acquisition activities may be synchronized such that sensors on an adjacent or second transducer array 120 may acquire stimulus originating from a first transducer array 118. A processing module 126 (similar to processing module 20) will setup the required activities of each NDM (stimulate or acquire) then provide a synchronization signal to all NDMs to start their respective activities. The process to acquire all the paths between sensors on adjacent transducer arrays is exactly the same as described above. Each sensor on the array boundary is stimulated, then each adjacent array quadrant is acquired, exactly the same as illustrated in FIG. 11.

Each NDM accomplishes the passive mode, i.e. listening to the structure for impact or stress events, almost approaching real-time, in exactly the same manner as the active mode only no stimulus is used. The advantage of using the passive method is that it is much faster than the active mode. A complete scan of a transducer array can be accomplished in 2.7 ms, and given the independence of the NDMs in the SHM System architecture of the present invention, all sensors can be scanned in 2.7 ms. Most impact or stress events of damage magnitude occur over tens to hundreds of milliseconds, so several scans will be made of the structure during these events eliminating the possibility of missing a damaging stress or impact event.

FIG. 13 illustrates an example of pulse—echo acquisition, when the NDM acquires signals produced by a stimulated sensor after the stimulus has ended. This is known as Pulse- Echo acquisition. This mode provides information about edges near the stimulated sensor and also the condition of the sensor itself. Instead of acquiring the wave data at another sensor, the wave data is an echo or reflected wave from an edge of the structure.

The NDM acquires data whose signal dynamic range is greater than 65 dB under these circumstances. To do this, the NDM employs switchable gain stages, reducing the gain (Av=0.1) during the stimulus generation time, then increasing the gain (Av=25) during the "listening" time, acquiring data during the entire activity. The health of each stimulated sensor can be determined by analyzing the pulse-echo data, thus allowing automatic detection of failed sensors. The NDM automatic acquires Pulse-Echo data every time a stimulus is generated.

The method and system of the present invention is advantageous over prior art systems in that the present invention provides for the simultaneous capture of sensor data from sensor arrays reducing acquisition time. Hence, fast damage detection is achieved while minimizing the cost, weight and size of the system. Furthermore, the present invention can monitor and inspect large areas of a structure, such as a wing of an aircraft.

While the present invention is described above with respect to what is currently considered its preferred embodiments, it is to be understood that the invention is not limited to that described above. To the contrary, the invention is intended to cover various modifications and equivalent arrangements within the spirit and scope of the appended claims.

What is claimed is:

1. A method for monitoring a structure for damage, comprising:
   stimulating a sensor in a sensor array to generate a plurality of waves, wherein the sensor array includes one or more quadrants, wherein each quadrant includes one or more sensors;
   acquiring sensor data from all sensors in each quadrant in parallel, the sensor data including one or more wave characteristics;
   processing the sensor data wave characteristics for analysis;
   comparing the processed sensor data wave characteristics with threshold values to determine the presence of damage to the structure; and
   notifying a corrective system if the presence of damage is determined, for corrective action.

2. The method of claim 1, wherein the sensor data is a series of data samples representing a wave captured over a period of time.

3. The method of claim 1, wherein the wave is propagated over the surface of the structure.

4. The method of claim 1, wherein interrogation time is independent of the number of sensor arrays.

5. The method of claim 1, wherein each sensor in the sensor array is stimulated.

6. The method of claim 1, wherein each sensor is a transducer.

7. The method of claim 1, further comprising multiplexing the sensor data from each quadrant into a single channel.

8. The method of claim 7, wherein the sensor data for each path from each quadrant is acquired simultaneously.

9. The method of claim 8, further comprising transmitting sensor data using a plurality of single channels from each quadrant to a computational engine where the data is compared with threshold values stored in a processing module.

10. The method of claim 9, wherein the structure has a plurality of sensor arrays; wherein each sensor in each of the sensor arrays is stimulated; and wherein the sensor data from all sensors in the sensor arrays are collected and used to determine the presence of damage on the structure.

11. The method of claim 9, wherein damage occurs when the sensor data is equal to or greater than the threshold values.

12. The method of claim 11, wherein the structure is between at least two adjacent transducer arrays; and wherein the at least two adjacent transducer arrays are stimulated simultaneously.

13. A method for monitoring a structure for damage, comprising:
   (a) laying out a plurality of sensor arrays on the structure; wherein each of the plurality of sensor arrays includes a plurality of quadrants; wherein each quadrant in the plurality of quadrants includes a plurality of sensors;
   (b) continuously acquiring sensor data from all sensors in each quadrant in parallel, wherein sensor data including one or more wave characteristics;
   (c) processing the sensor data wave characteristics for analysis;
   (d) comparing the processed sensor data wave characteristics with threshold values to detect damage to the structure;
   (e) repeating steps (b)-(d) so as to detect damage to the structure; and
   (f) notifying a corrective system if the damage to the structure is detected, for corrective action.

14. The method of claim 13, wherein each sensor is a transducer.

15. The method of claim 13, further comprising multiplexing the sensor data from each of the quadrant into a plurality of single channels with a single channel for each quadrant.

16. The method of claim 15, wherein the sensor data from each quadrant is acquired simultaneously.

17. The method of claim 16, further comprising transmitting the sensor data using the plurality of single channels from each quadrant to a computational engine where the sensor data is compared with threshold values stored in a processing module.

18. The method of claim 17, wherein damage occurs when the sensor data is equal to or greater than the threshold values.

19. A system for monitoring a structure for damage, comprising:
   a plurality of sensor arrays on the surface of the structure; wherein each sensor array in the plurality of sensor arrays includes a plurality of quadrants; and wherein each quadrant in the plurality of quadrants includes a plurality of sensors; and
   a plurality of network detection modules; wherein each network detection module in the plurality of network detection modules acquires sensor data from all sensors in each quadrant in parallel, the sensor data including one or more wave characteristics; wherein each network detection module includes a plurality of multiplexers for multiplexing the sensor data from each quadrant for transmission into a plurality of single channels with a single channel for each quadrant and a computational engine for comparing the wave characteristics from the plurality of single channels with predetermined thresholds to determine the presence of damage to the structure.

20. The system of claim 19, wherein the sensor data is a series of data samples representing a wave captured over a period of time.

21. The system of claim 20, wherein the wave is propagated over the surface of the structure.

22. The system of claim 19, wherein interrogation time is independent of the number of sensor arrays.

23. The system of claim 19, wherein each sensor in the sensor array is stimulated.

24. The system of claim 19, wherein each sensor is a transducer.

25. The system of claim 19, wherein each multiplexer multiplexes the sensor data from one of the quadrant into a single channel.

26. The system of claim 25, wherein a path data from each quadrant is acquired simultaneously.

27. The system of claim 26, wherein the sensor data is transmitted using single channel each quadrant to a computational engine where the sensor data is compared with threshold values stored in a processing module.

28. The system of claim 27, wherein damage occurs when the sensor data is equal to or greater than the threshold values.

29. A system for monitoring a structure for damage, comprising:

a plurality of sensor arrays disposed about the boundaries of the structure and between the boundaries of the structure; wherein each sensor array in the plurality of sensor arrays includes a plurality of quadrants; and wherein each quadrant in the plurality of quadrant includes a plurality of sensors; and a plurality of network detection modules; wherein each network detection module in the plurality of network detection modules acquires sensor data from all sensors in each quadrant in parallel, the sensor data including one or more wave characteristics; where each of the network detection modules are synchronized causing sensors on a first sensor array on a first boundary of the structure to acquire stimulus originating from a second sensor array on a second boundary of the structure; wherein each network detection module includes a plurality of multiplexers for multiplexing the sensor data from each quadrant into a plurality of single channels with a single channel for each quadrant and a computational engine for comparing the wave characteristics from the plurality of single channels with predetermined thresholds to determine the presence of damage to the structure.

* * * * *